United States Patent [19]

Zobel

[11] Patent Number: 4,702,229

[45] Date of Patent: Oct. 27, 1987

[54] ENDOSCOPE WITH A MEASURING DEVICE

[75] Inventor: Jürgen Zobel, Bretten-Sprantal, Fed. Rep. of Germany

[73] Assignee: Richard Wolf GmbH, Knittlingen, Fed. Rep. of Germany

[21] Appl. No.: 844,191

[22] Filed: Mar. 26, 1986

[30] Foreign Application Priority Data

Apr. 6, 1985 [DE] Fed. Rep. of Germany ....... 3512602

[51] Int. Cl.$^4$ ............................................. A61B 1/00
[52] U.S. Cl. ........................................... 128/4; 128/6
[58] Field of Search ...................... 128/4, 6; 350/96.26

[56] References Cited

U.S. PATENT DOCUMENTS 3,595,220 7/1971 Kawahara ................................. 128/6
4,558,691 12/1985 Okada ..................................... 128/6

Primary Examiner—William H. Grieb
Attorney, Agent, or Firm—Hill, Van Santen, Steadman & Simpson

[57] ABSTRACT

An endoscope is disclosed for determining the size of an object in a cavity, for example in a human or animal body or in a machine. The endoscope comprises an optical system for viewing the object laterally from its distal end. The transmission system has an image plane, visible through an eyepiece, on which a measuring scale is provided. By viewing a selected part of the object simultaneously or successively from two different angles, with a predetermined distance between their vertices, at a constant lateral distance from the endoscope, images of the object can be seen at two different positions on the measuring scale, from which the size of the object can be calculated.

6 Claims, 4 Drawing Figures

ENDOSCOPE WITH A MEASURING DEVICE

BACKGROUND OF THE INVENTION

The invention relates to an endoscope for determining the size of objects present in cavities, of human, animal or machinary bodies, comprising an optical image transmission system and a system for establishing the distance between the object to be examined and the distal endoscope extremity, wherein the momentary distance is the criterion for determining the reproduction factor of a measuring scale and the measuring scale present in a reproduction plane of the image transmission system is visible through the eyepiece.

DESCRIPTION OF THE PRIOR ART

In the case of endoscopes of the aforesaid type, e.g. according to DE-AS-1,766,904, an illuminated object is scanned punctiformly by a light beam within the field of view of the optical system of an endoscope and in the case of changes in distance travels over a measuring scale observable through the eyepiece of the optical system, whereby it is possible to determine the distance of the object from the distal endoscope extremity, and the scale divisions represent a criterion for determining the reproduction factor. In this connection, it is necessary—apart from an illumination of the field of view and apart from the viewing optical system for generation the light spot in the field of view of the optical system—that a complementary light guide with appropriate cable joints for a spot light should be led through the endoscope, so that the endoscope has a comparatively complex structure.

SUMMARY OF THE INVENTION

The object of the invention consists in substantially simplifying the structure of an endoscope and in particular of a technoscope of the kind referred to in the foregoing, so that dimensions of the object may be determined by measuring the distance of an object from the endoscope.

In accordance with the invention, this object is achieved in the case of the endoscope referred to in the foregoing, by the fact that the optical sytem for observation of the object is so organised that a selected section of the object may be observed from two different angles, the distance between the vertices of these angles being fixedly preset.

To this end, the procedure advantageously adopted is that an outer shaft is primarily fixedly joined to the object under utilisation of the endoscope as a rigid technoscope, and that an inner shaft is axially displaceable within the outer shaft through the said fixedly preset length, in such a manner that the object may be observed consecutively from two different angles and the image is depicted on a measuring scale observable through the eyepiece, the deflection of the image forming a criterion for the distance of the object from the objective and also allows of determining the object dimensions under utilisation of the known data of the endoscope.

As an alternative, the inner shaft may be provided with a partially transparent mirror distally behind the objective lens of the optical system and with a reflecting mirror at the said fixed distance, so that two images of the object may be engendered at the same time and compared on a measuring scale by means of the eyepiece, so that the spacing of the two images produced then provides a criterion for the distance of the object from the distal endoscope extremity and for calculation of the object dimensions.

Further objects and advantages of the invention will become apparent from the following detailed description taken in conjunction with the accompanying drawings which illustrate preferred embodiments thereof.

DETAILED DESCRIPTION OF THE PREFERRED EMBODIMENTS

Figure 1:
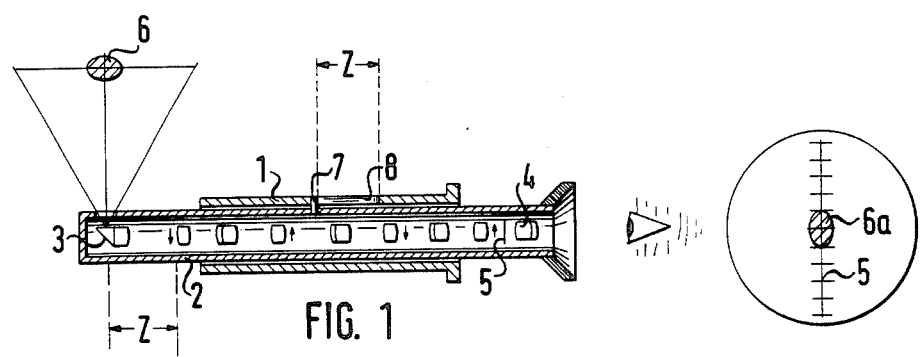
FIG. 1 shows a longitudinal cross-section of the endoscope in a first position of the axially displaceable optical system having a lateral objective, and with a plan view of the measuring scale observable through the eyepiece of the optical system.
Figure 2:
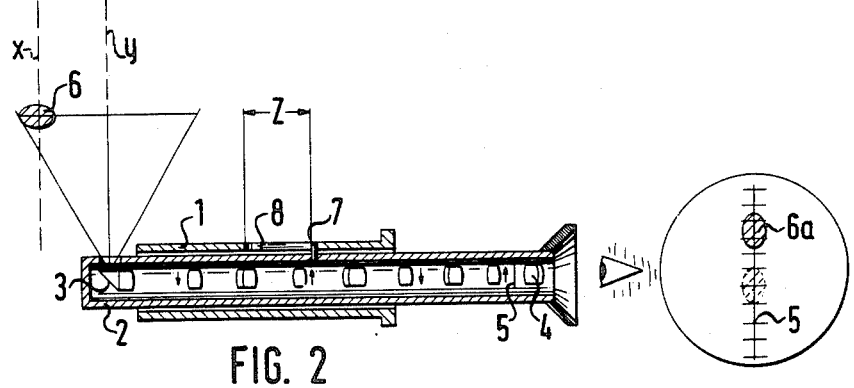
FIG. 2 shows the same longitudinal cross-section in a second proximally displaced position of the optical system with the corresponding measuring scale.

According to the example in FIGS. 1 and 2, the endoscope is a rigid endoscope comprising an outer shaft 1 which, if the endoscope is utilised as a technoscope, is fixedly connected to a technical object, e.g. an engine. An inner shaft 2 receiving the optical system is axially displaceable in the outer shaft 1 by means of a drive and is provided at its distal end beyond the outer shaft with a reflector 3 for lateral viewing as well as with a measuring scale 5 to be observed via the eyepiece 4 at a proximal end of the shaft. The reflector 3 having, which has a lateral field of view preferably at right angles to the optical axis and aimed at a prominent part 6 of an object, assumes a position x as shown in FIG. 1, which is distally delimited by a stop, e.g. by a pin 7 of the shaft 2, which passes through an elongated slot 8 of the outer shaft 1 and as shown in FIG. 1 is positioned against the distal extremity of the slot 8. At this position, the image 6a of the object section 6 observed, is situated at the centre of the scale 5, for example. To determine the distance of the object section 6 from the reflector 3, the inner shaft is moved in a proximal direction to the position y according to FIG. 2 until the pin 7 strikes against the proximal extremity of the slot 8, so that the object section 6 is then laterally situated with respect to the objective axis, so that the image 6a of this object section has moved to a second position on the scale 5 and the image deflection may be read off the scale 5. The measurement is then performed, e.g. by placing an edge of an object defect according to FIG. 1 in the vertical objective axis and by immobilising the endoscope in this position. The inner shaft 2 is thereupon displaced in the proximal direction by the fixed distance value z between the positions x and y, the fixed point 6 equally being displaced in image form through a particular number of scalar divisions of the scale 5, so that the number of scalar divisions then forms a criterion for calculation of the object distance and of the object dimensions. The length of displacement z, the focal length of the optical system and the angle between the connection of the reflector 3 and the object point 6 and the vertical objective axis are now known, so that the object distance and the reproduction scale of the scale are established thereby and the corresponding value of the object dimensions may be read off this scale.

Figure 3:
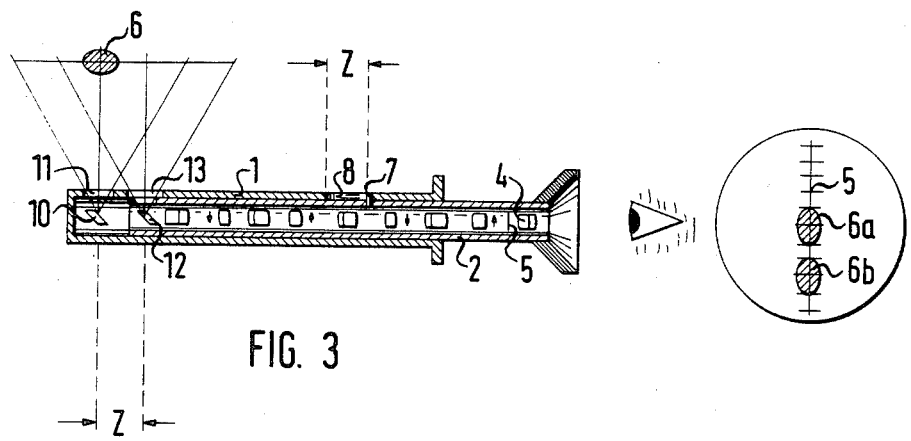
FIG. 3 shows a longitudinal cross-section of a modified endoscope comprising two reflectors placed one behind another with a lateral objective and a corresponding measuring scale in enlarged plan view.
Figure 4:
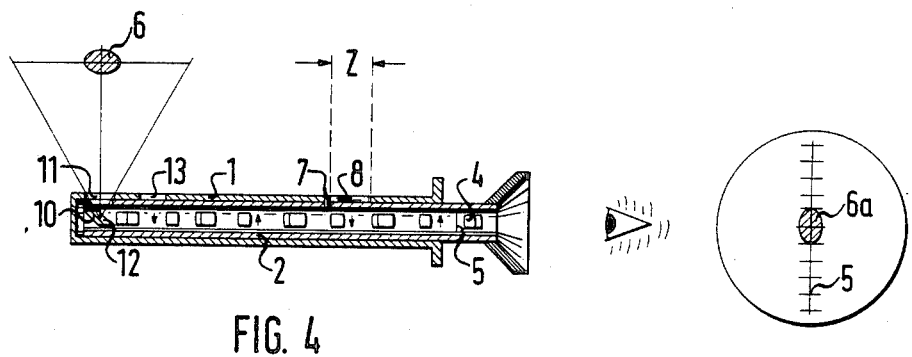
FIG. 4 shows the same cross-section as depicted in FIG. 3, with the reflectors pushed together and the corresponding measuring scale in plan view.

A second solution for determining object size according to FIGS. 3 and 4 is particularly suited for endoscopy in human bodily cavities. The endoscope is constructed practically according to the form according to FIGS. 1 and 2, and identical parts are denoted by the same reference symbols.

In this case however, the outer shaft 1 projects distally beyond the inner shaft 2. In the distal extremity of the outer shaft 1 is situated a reflector 10 sloping with respect to the optical axis and having a lateral objective aperture 11, so that a prominent object section 6 may be projected as an image by means of the optical system, on to the measuring scale 5 and observed via the eyepiece 4. The viewing axis via the reflector 10 is advantageously set at right angles to the axis of the optical system, so that the subsequent calculations are also facilitated thereby.

A second partially transparent reflector 12 placed at a fixed distance z in a proximal direction from the reflector 10 is distally provided within the inner shaft 2 with a lateral objective 13. The reflector 12 has the same angle to the optical axis as the reflector 10.

The reflector 10 then generates an image 6a of the illuminated object section 6 on the measuring scale 5, and the partially transparent reflector 12 generates a second image 6b set at a distance from the image 6a on the scale 5. This distance between the two images 6a and 6b may be read off the scale 5, and reproduces a criterion for the distance of the object 6 from the distal endoscope extremity. The object dimensions may then again be determined trigonometrically as in the embodiment of FIGS. 1 and 2.

As shown in FIG. 4, it is also possible to displace the inner shaft together with the partially transparent reflector 12 axially in a distal direction until the two reflectors 10 and 12 are in coincidence, so that after retracting the inner shaft through the distance z, it is possible to operate precisely as described with reference to FIGS. 1 and 2.

What is claimed is:

1. In an endoscope for determining the size of an object present in a cavity, said endoscope comprising an optical transmission system with an optical axis, a proximal eyepiece and an objective arranged to view said object laterally to said axis from a distal part of the endoscope, a measuring scale being visible through said eyepiece and being situated in an image plane of said transmission system and means for establishing the distance between said object and said distal part of the endoscope, said distance representing the criterion for calibrating said measuring scale, an improvement comprising said optical transmission system being adjustable to enable a selected part of said object to be viewed laterally by the objective from two different angles at a constant lateral object distance from the endoscope with the distance between the two vertices of said two angles being fixedly preset.

2. In an endoscope for determining the size of an object present in a cavity, said endoscope comprising an optical transmission system with an optical axis, a proximal eyepiece and an objective arranged to view said object laterally to said axis from a distal part of the endoscope, a measuring scale being visible through said eyepiece and being situated in an image plane of said transmission system and means for establishing the distance between said object and said distal part of the endoscope, said distance representing the criterion for calibrating said measuring scale, the improvements comprising means of adjusting the optical transmission system to enable a selected part of said object to be viewed laterally by the objective from two different angles at a constant lateral object distance from the endoscope with the distance between the two vertices of said two angles being fixedly preset, said means for adjusting including at least said objective being axially displaceable by a length corresponding to the said distance between the two vertices of said two angles relative to a fixed endoscope section which is held stationary with respect to the object to be measured.

3. An endoscope as claimed in claim 2, wherein the fixed endoscope section is formed by an outer shaft which is immobilisable with respect to the object to be measured, and wherein the lateral objective is carried by an inner shaft which is axially displaceable within said outer shaft by said preset distance.

4. An endoscope as claimed in claim 3, characterized in that the inner shaft receives the whole image transmission system including the lateral objective and has a substantially hollow cylindrical shape being closed off at its distal extremity by means of a transverse wall.

5. In an endoscope for determining the size of an object present in a cavity, said endoscope comprising an optical transmission system with an optical axis, a proximal eyepiece and an objective arranged to view said object laterally to said axis from a distal part of the endoscope, a measuring scale being visible through said eyepiece and being situated in an image plane of said transmission system and means for establishing the distance between said object and said distal part of the endoscope, said distance representing the criterion for calibrating said measuring scale, the improvements comprising said optical transmission system being adjustable to enable a selected part of said object to be viewed lateral from two different angles at a constant lateral object distance from the endoscope with the distances between the two vertices of said two angles being fixedly preset, and said optical transmission system having first and second reflectors situated on the same axis as the objective, said reflectors being positioned mutually parallel and sloping at the same angle to the said axis, the first reflector being positioned proximally relative to the second reflector and being partially transparent with an axial distance between the two reflectors corresponding to the said distance between the two vertices of the two angles.

6. An endoscope as claimed in claim 5, wherein said first reflector and the rest of the optical image transmission system are fixedly installed in an inner shaft which is slidably received in an outer shaft having at its distal end first and second axially spaced lateral apertures, said second reflector being secured in said outer shaft and optically aligned with said second aperture and said inner shaft being axially movable between a first position in which said first reflector is aligned with said first aperture and a second position in which both said reflectors are aligned with said second aperture.

* * * * *